(12) United States Patent
Quinn et al.

(10) Patent No.: US 6,652,474 B1
(45) Date of Patent: *Nov. 25, 2003

(54) ANKLE BRACE

(75) Inventors: Patrick J. Quinn, 762 Camberwell Dr., Eagan, MN (US) 55123; Gregory A. Hoistad, 7101 W. 113 St., Bloomington, MN (US) 55438; Frank W. Campbell, Oakdale, MN (US)

(73) Assignees: Patrick J. Quinn, Eagan, MN (US); Gregory A. Hoistad, Bloomington, MN (US)

( * ) Notice: Subject to any disclaimer, the term of this patent is extended or adjusted under 35 U.S.C. 154(b) by 315 days.

This patent is subject to a terminal disclaimer.

(21) Appl. No.: 09/692,637

(22) Filed: Oct. 19, 2000

Related U.S. Application Data

(63) Continuation-in-part of application No. 09/430,007, filed on Oct. 29, 1999.

(51) Int. Cl.[7] .................................................. A61F 5/00
(52) U.S. Cl. ........................... 602/21; 602/5; 602/23; 602/27; 602/29; 602/60; 602/65; 128/882
(58) Field of Search ............................. 602/5, 21, 23, 602/27–29, 60–63, 65; 128/882

(56) References Cited

U.S. PATENT DOCUMENTS

| | | |
|---|---|---|
| 1,374,669 A | 4/1921 | McClellan |
| 2,450,862 A | 10/1948 | Wilkinson .................... 128/80 |
| 3,327,410 A | 6/1967 | Park, Sr. et al. ................ 36/2.5 |
| 3,613,273 A | 10/1971 | Marquis ........................ 36/2.5 |
| 3,674,023 A | 7/1972 | Mann .......................... 128/166 |
| 3,970,083 A | 7/1976 | Carrigan ...................... 128/166 |
| 4,133,311 A | 1/1979 | Karczewski ................. 128/166 |
| 4,323,058 A | 4/1982 | Detty ........................... 128/80 |
| 4,527,556 A | 7/1985 | Nelson ......................... 128/80 |
| 4,869,267 A | 9/1989 | Grim et al. .................... 128/80 |
| 4,878,504 A | 11/1989 | Nelson ......................... 128/80 |
| 5,067,486 A | 11/1991 | Hely ............................ 128/80 |
| 5,217,431 A | 6/1993 | Toronto et al. ............... 602/27 |
| 5,445,598 A * | 8/1995 | Nguyen-Senderowicz ... 602/65 |
| 5,795,316 A | 8/1998 | Gaylord ....................... 602/27 |
| 5,899,872 A | 5/1999 | Gilmour ....................... 602/65 |
| 6,117,098 A | 9/2000 | Weber et al. .................. 602/27 |
| 6,398,750 B1 * | 6/2002 | Quinn et al. .................. 602/65 |
| 2002/0058895 A1 * | 5/2002 | Quinn et al. .................. 602/65 |

* cited by examiner

Primary Examiner—Nicholas D. Lucchesi
Assistant Examiner—L. Amerson
(74) Attorney, Agent, or Firm—IPLM Group, P.A.

(57) ABSTRACT

An ankle support (10) includes a first portion (11), which is a boot-like member, and an outer member (30). A pre-configured figure eight member comprising a strap (240) is positioned around the boot-like member (11). The outer member (30) is secured to the boot-like member (11) and forms a cover to hold the pre-configured figure eight member in place to prevent misalignment of the strap (240).

15 Claims, 7 Drawing Sheets

ANKLE BRACE

This patent application is a continuation-in-part of U.S. patent application Ser. No. 09/430,007 for ANKLE BRACE, which was filed on Oct. 29, 1999.

BACKGROUND OF THE INVENTION

1. Field of the Invention

This invention relates generally to an ankle brace and more particularly to an ankle brace having an internal pre-configured figure eight member.

2. Description of the Prior Art

Providing ankle supports for athletes engaging in various sporting activities is well known. This protection supports the ankle in such a manner to lock the heel against turning, as this may cause the ankle to be strained or sprained. Various forms of protection are used to prevent injuries in addition to providing protective support for ankles that have already been injured.

Ankle braces, such as those shown in U.S. Pat. No. 4,527,556 provide an easy-to-use brace for supporting the ankle. Also, a heel may be locked in place by the use of adhesive tape to securely tape the ankle. This is done in a "figure eight" pattern. There are a number of disadvantages in using tape. One of the major disadvantages is the large cost that is associated with taping an ankle each day. Other disadvantages include slippage of the tape when the wearer perspires, stretching or loosening of the tape during use, the development of calluses on the foot and ankle, and the burden of having to clean the ankle or foot after the tape is removed. Elastic bandages have been used, but these do not provide as much support as the adhesive tape. Other ankle braces, such as those shown in U.S. Pat. No. 5,067,486 utilize an ankle brace that incorporates two straps that may be wrapped around the brace in the form of a figure eight. The use of such straps in conjunction with ankle braces is known, which is further shown in U.S. Pat. No. 3,073,305.

One of the major disadvantages with braces that incorporate such straps is that the straps are always loose and easily become entangled. This is especially true with the common use of Velcro®-type fasteners where the fastening ends of the straps may become attached to any portion of the brace or a duffel bag in which they may be stored. This provides a great source of frustration when using the brace. When the brace is taken off, the straps are in disarray and it is cumbersome and time-consuming to straighten out the straps so that they may later be wrapped around the ankle. Further, the user-has to position the straps correctly about the foot and the ankle.

The present invention addresses the problems associated with the prior art and provides for an easy-to-use ankle brace, which incorporates a pre-configured figure eight member.

SUMMARY OF THE INVENTION

In a preferred embodiment ankle support for use in supporting an ankle bone and an ankle joint, the ankle support includes a boot-like member, a pre-configured FIG. eight member, and an attachment. The boot-like member has a sleeve portion for receiving a foot and an ankle, and the boot-like member is securable about the foot and the ankle. The boot-like member includes a first side, a second side, a top, and a back portion. The pre-configured figure eight member includes a first portion having a first end and a second portion having a second end. The first end is releasably secured to the first side of the boot-like member and the first portion is positioned under the foot and extends over the top of the boot-like member and proximate the back portion. The second end of the strap is releasably secured to the second side of the boot-like member and the second portion is positioned under the foot and extends over the top of the bootlike member and proximate the back portion. The attachment is positioned to keep the strap positioned proximate the boot-like member. More specifically, the attachment is positioned between the first end and the second end of the strap, wherein the pre-configured figure eight is formed by the strap and the attachment maintains the strap in position.

In another preferred embodiment, an ankle support for use in supporting an ankle bone and an ankle joint includes a boot-like member, a pre-configured figure eight member, and an outer member. The boot-like member has a sleeve portion for receiving a foot and an ankle, and the boot-like member is securable about the foot and the ankle. The boot-like member includes a first side, a second side, a top, and a back portion. The pre-configured figure eight member has a first end and a second end. The first end is releasably secured to the first side of the boot-like member, and the pre-configured figure eight member extends under the foot and over the top of the boot-like member where it wraps around the ankle proximate the back portion. Then, the pre-configured figure eight member continues over the top of the boot-like member and under the foot and then along the second side where the second end is releasably secured thereto. The outer member is secured to the boot-like member, and the outer member forms a cover to hold the pre-configured figure eight member in place and prevent misalignment of the figure eight member.

DETAILED DESCRIPTION OF THE PREFERRED EMBODIMENT

Figure 1:
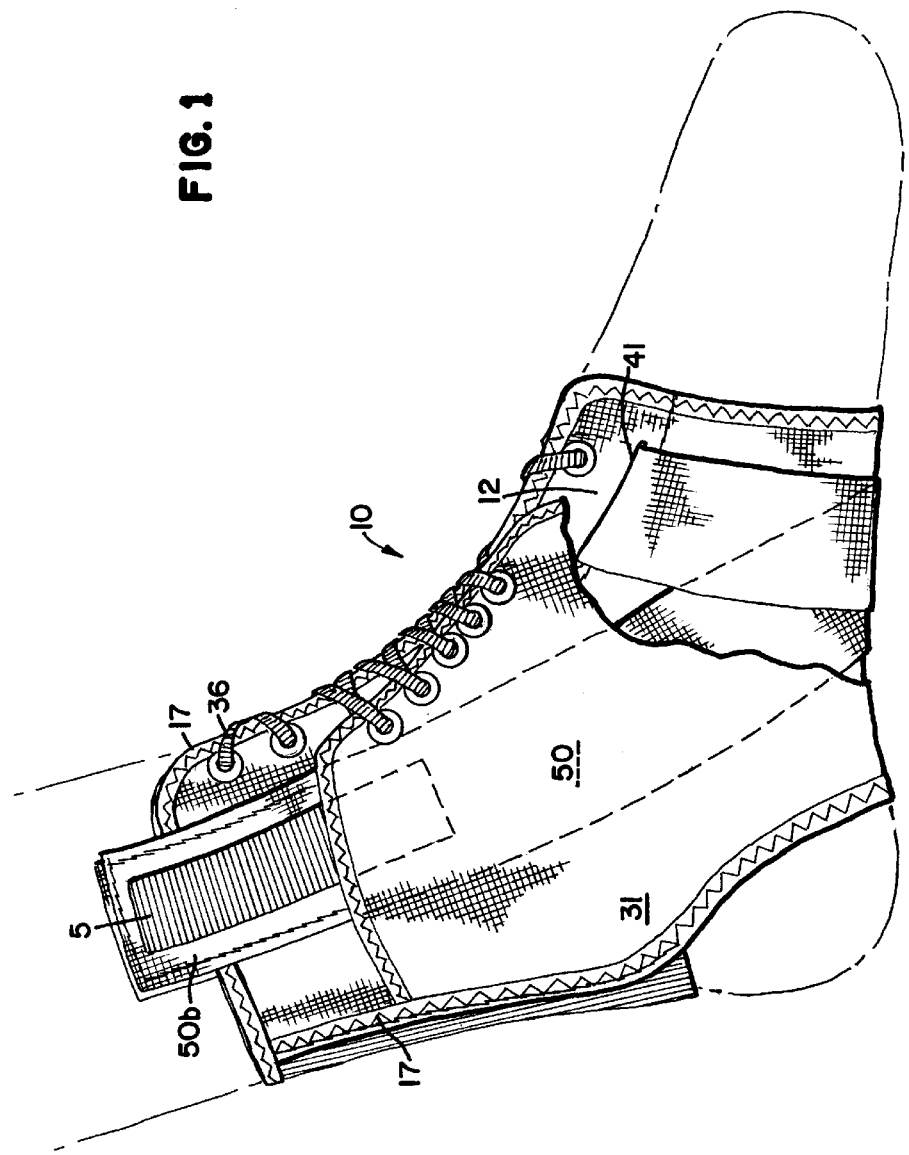
FIG. 1 is a side elevational view of an ankle support brace incorporating the present invention.
Figure 2:
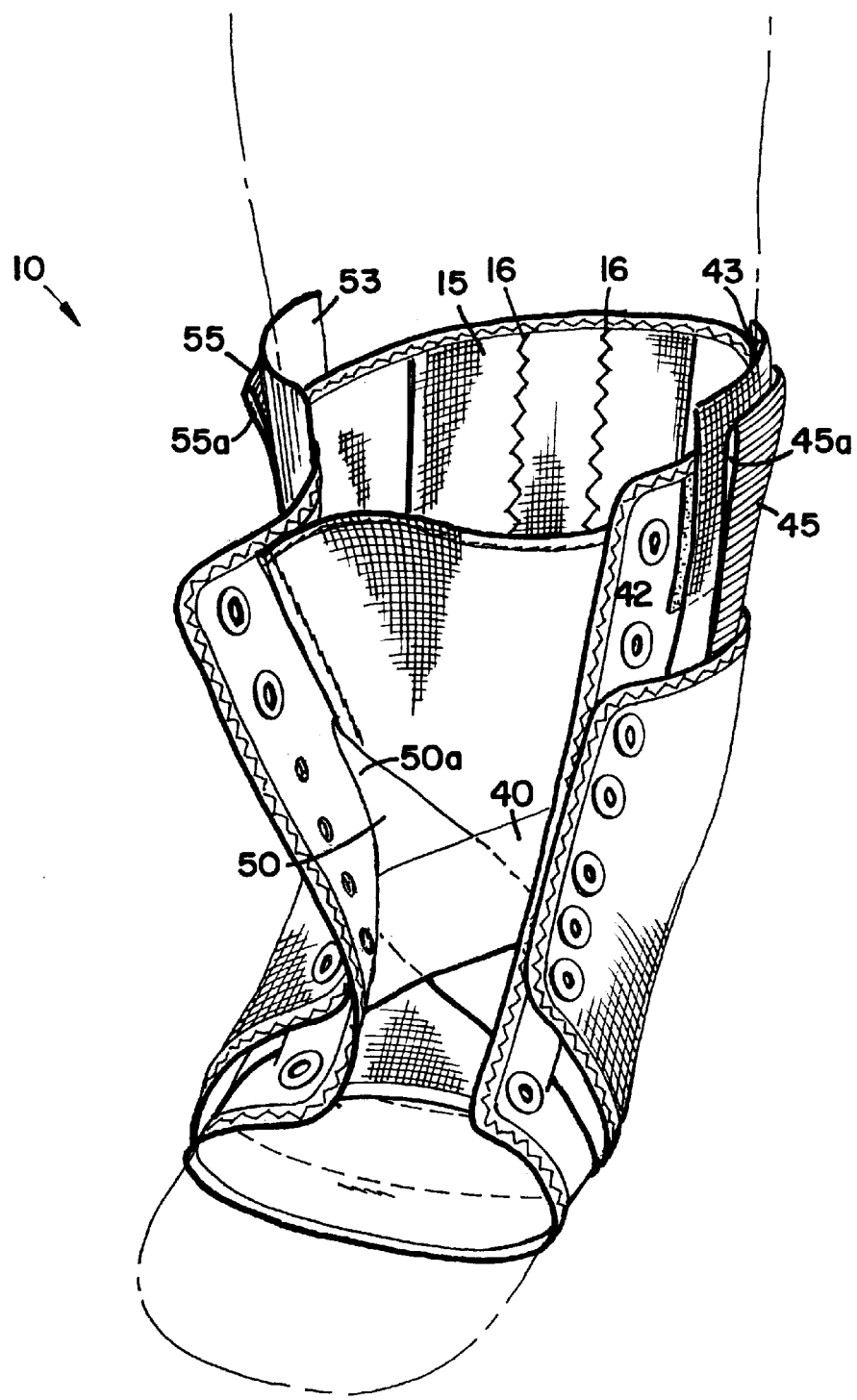
FIG. 2 is a perspective view generally viewed from the front of the ankle support brace of FIG. 1.

Referring to the drawings, wherein like numerals represent like parts throughout the several views, an ankle support brace constructed according to the principles of the present invention is designated by the numeral 10.

Figure 4:
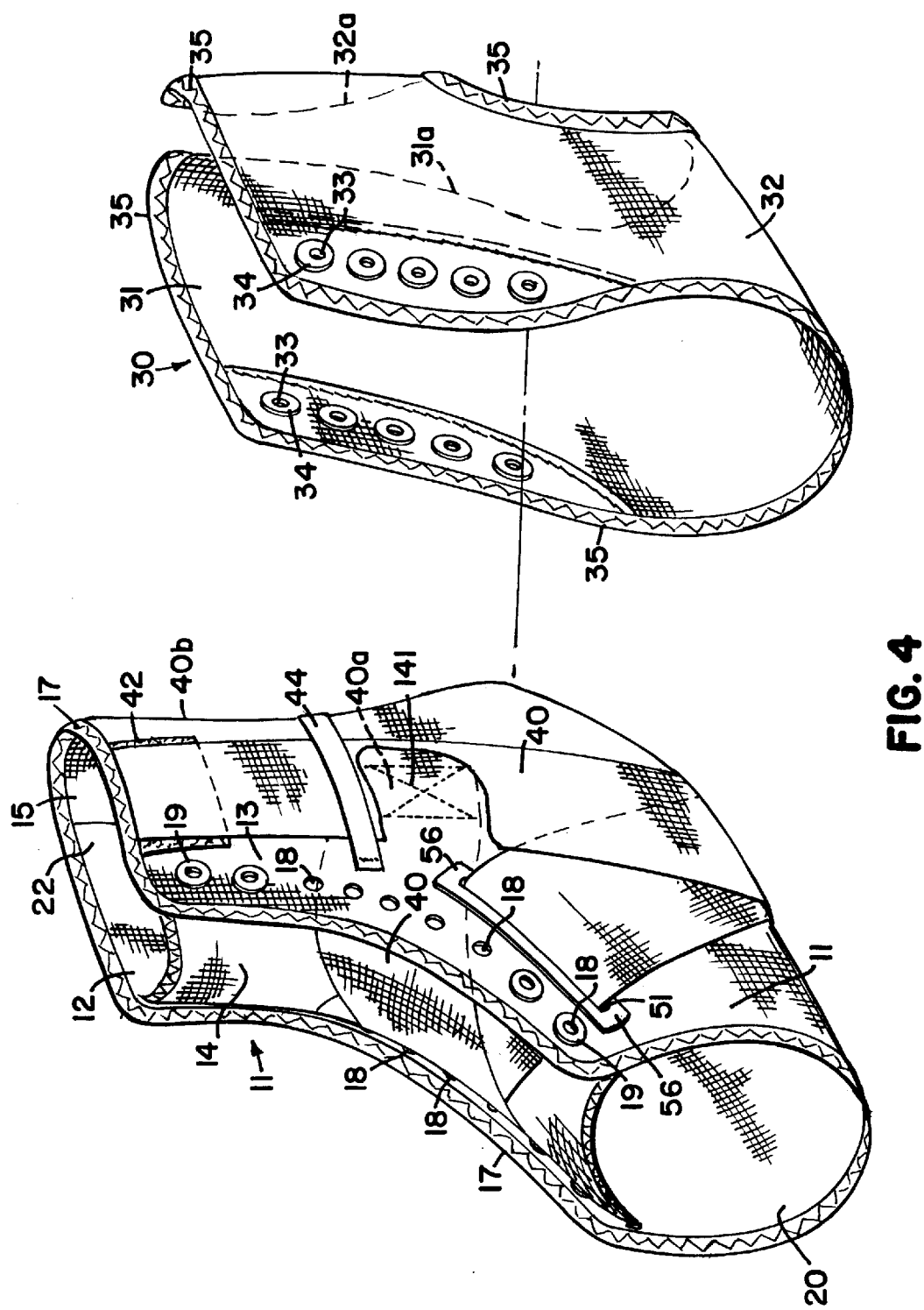
FIG. 4 is an exploded perspective view showing the ankle support brace of FIG. 1.

In a first preferred embodiment, the ankle support 10 has a first portion 11 and an Outer member 30, which are shown more particularly in FIG. 4. The first portion 11 and outer member 30 may be made of suitable material such as 840 denier nylon or a combination nylon and polymesh covered with a vinyl coating. Further, a suitable foam padding material may be laminated to the first portion 11 and would be positioned proximate the inner side which comes in contact with the leg or ankle.

The first portion 11 forms a boot-like member, which encircles the ankle to be supported. The first portion 11 has a right side 12 and a left side 13 and is preferably formed from a one-piece material. The right side 12 is operatively connected to the left side 13 at the front by a stretchable mesh tongue 14. The mesh tongue is connected to the first portion 11 by suitable means such as stitching. The rear portions of the right side 12 and the left side 13 are connected by an elastic member 15 by suitable means such as stitching 16. The elastic member 15 provides for some expansion between the spaced apart back edges of the right side 12 and left side 13. A binding 17 is secured around the periphery of the first portion 11. The binding may be of suitable material such as a polyester binding tape. A plurality of openings 18 are formed along the front portions of the right side 12 and the left side 13. Eyelets 19 are secured to the top two and the bottom two openings 18. The first portion 11 forms three openings. The first opening 20 is positioned proximate the toes of the user. The second opening 21 is the heel opening. The third opening 22 is formed at the top of the first portion 11 and is formed for the lower part of the leg of the user proximate the ankle.

The outer member 30, as most clearly shown in FIG. 4, has a right side 31 and a left side 32. At the front of both the right side 31 and the left side 32 are formed a plurality of openings 33 around which eyelets 34 are secured. A binding 35 is secured by suitable means such as stitching to the top and the front of sides 31 and 32. The bottom U-shaped portion of the back also has binding 35 secured thereto. The upper rear edges 31a and 32a of right side 31 and left side 32 are secured to the first portion 11 by stitching. They are secured to the first portion 11 before the binding 17 is applied to the back side of the right side 12 and left side 13. This therefore secures the back side of the outer member 30 to the first portion 11. The front portion of the outer member 30 and the first portion 11 are operatively connected by means of laces 36. Preferably, the eyelets 34 are slightly offset from the openings 18 to provide a more secure fit as taught by U.S. Pat. No. 4,527,556. The ankle support 10 described thus far is typical of a prior art ankle support already available.

Figure 6:
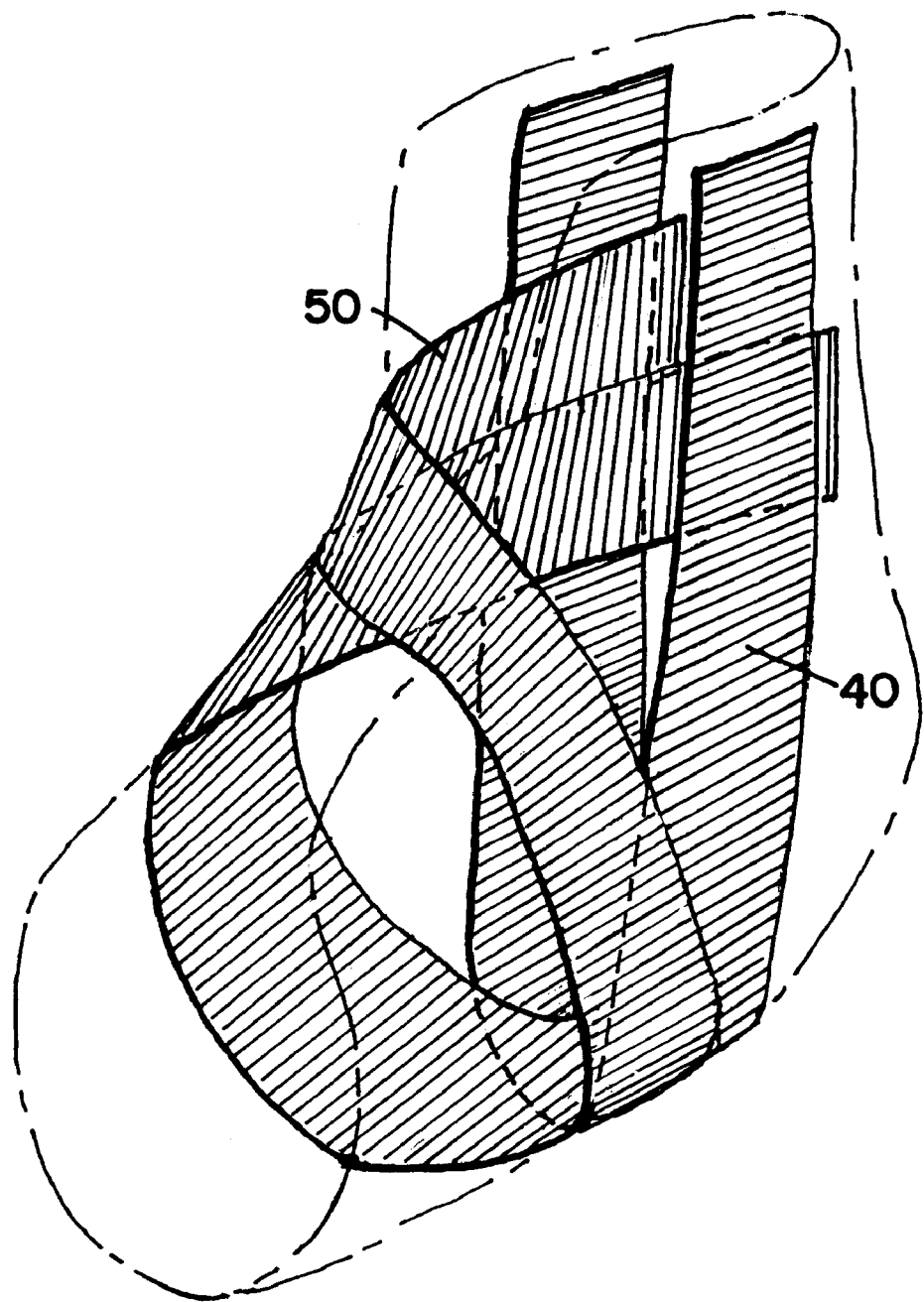
FIG. 6 is a perspective view, shown generally from the left side, of the straps of the ankle support brace of FIG. 1 and FIG. 5.

The present invention also provides a pre-configured or internal figure eight member in an ankle support design, as shown in FIG. 6. In the first preferred embodiment, the pre-configured figure eight member includes a first strap 40 which has a first end 40a secured to the inside surface of the left side 13 by suitable means such as stitching 141. The first strap 40 is then positioned between the inside surface of the left side member 13 and the mesh tongue 14. The first strap 40 is in position before the tongue 14 is secured to the left side. Therefore, when the tongue is stitched to the left side 13, the strap 40 is also stitched between the tongue 14 and left side 13. The first strap 40 then continues over the top portion of the foot and goes through a slot 41 which is formed in the right side 12, at a position just slightly above the position where the tongue 14 and right side 12 are joined. The strap 40 then goes underneath the foot and back up the left side 13. A rectangular pad of hook material 42 is sewn to the left side 13 proximate the top of the left side 13. A loop material 43 is sewn to the inside surface of the second end 40b of the strap 40. The loop material 43 and hook material 42 provide for a releasable connection between the second end 40b of the strap 40 and the left side 13. The hook and loop material may be any suitable material such as Velcro® material, which is well known in the art. It is of course understood that other suitable means for releasably connecting the strap 40 may be utilized. An additional strap 44 is secured to the left side 13 by suitable means such as stitching. The strap 44 forms a loop through which the second end 40b is inserted and is used as an additional guide. The strap 44 is at an elevation which is approximately one inch below the top of the left side 32 of the outer member 30. Optionally, a tab 45 may be utilized. The tab 45 is secured at its bottom to the strap 40 and is free to move away from the strap 40 at the top end of the tab 45. At the top end of the tab 45 is an opening 45a through which a user may insert his or her fingers. The tab 45 is used to assist in pulling up the strap 40. However, it is appreciated that the tab 45 is optional and the user may simply pull up on the second end 40b of the first strap 40 to tighten the first strap 40. For clarity in viewing FIG. 4, the tab 45 has not been shown in FIG. 4.

The pre-configured figure eight member also includes a second strap 50 which has a first end 50a secured to the inside surface of the right side 12 by stitching (not shown). It is secured in the same manner as the first end 40a of the first strap 40. The second strap 50 is then positioned between the inside surface of the right side member 12 and the mesh tongue 14. The second strap 50 is in position before the tongue 14 is secured to the right side. Therefore, when the tongue is stitched to the right side 12, the strap 50 is also stitched between the tongue 14 and right side 12. The second strap 50 then continues over the top portion of the foot an goes through a slot 51 which is formed in the left side 13, at a position just slightly above the position where the tongue 14 and left side 13 are joined. The strap 50 is underneath the strap 40 when the straps cross at the top, as shown in FIG. 4. The strap 50 then goes underneath the foot and back up the right side 12. A rectangular pad of hook material, not shown but similar to material 42, is sewn to the right side 12 proximate the top of the right side 12. A loop material 53 is sewn to the inside surface of the second end 50b of the strap 50. The loop material 53 and hook material provide for a releasable connection between the second end 50b of the strap 50 and the right side 12. The hook and loop material may be any suitable material such as Velcro® material, which is well known in the art. It is of course understood that other suitable means for releasably connecting the strap 50 may be utilized. An additional strap, not shown, but similar to strap 44 is secured to the right side 12 by suitable means such as stitching. The strap forms a loop through which the second end 50b is inserted and is used as an additional guide. The strap is at an elevation which is approximately one inch below the top of the right side 31 of the outer member 30. Optionally, a tab 55 with an opening 55a may be used. The tab 55 is the same as tab 45 and so it will not be described further. However, it is appreciated that the tab is optional and the user may simply pull up on the second end 50b of the second strap 50 to tighten the first strap 50. A plastic loop guide 56 is secured to the outer side of the left side 13. The guide 56 has a slot which is positioned over the slot 51. The guide 56 prevents bunching of the support 10 from the force of the strap 50. A similar guide (not shown) is used proximate slot 41. The loop guide 56 helps prevent bunching up the straps 40 and 50 at the top of the brace, proximate the guides, when a pulling force is applied to the second ends 40a and 50a.

While it is preferred in the first preferred embodiment that the straps 40 and 50 be secured at their first ends to the side, it is understood that with other designs or other boot-like members, the first ends may be attached elsewhere, such as at the front or back. The first ends are secured at approximately the same height, which is proximate the malleoli, recognizing that the medial malleoli is higher than the lateral malleoli.

The first and second straps 40 and 50 form a pre-configured figure eight member, which is held in position by the outer member 30. The straps 40 and 50 are covered by the outer member 30. The outer member 30 prevents the straps from becoming snagged or caught on other objects. Further, it keeps the straps 40 and 50 in a pre-configured figure eight position. Therefore, there is no need for the user to apply the straps in a correct configuration since the design of the present invention keeps the straps 40 and 50 in the correct configuration of a figure eight. The figure eight configuration effectively locks the heel preventing inversion and eversion sprains. The support 10 is designed so that it may be utilized on either the right or left foot. Extra lateral or medial protection can be obtained by pulling the straps tighter. That is, pulling the medial strap and then the lateral strap will result in additional lateral protection and vice versa. The straps 40 and 50 are prevented from going out the front of the ankle support 10 by the laces which are laced through the eyelets and holes in the first portion 11 and outer member 30. The sewing of the outer member 30 to the first portion 11 prevents the straps from loosing their configuration by going out the rear of the ankle support 10.

Figure 3:
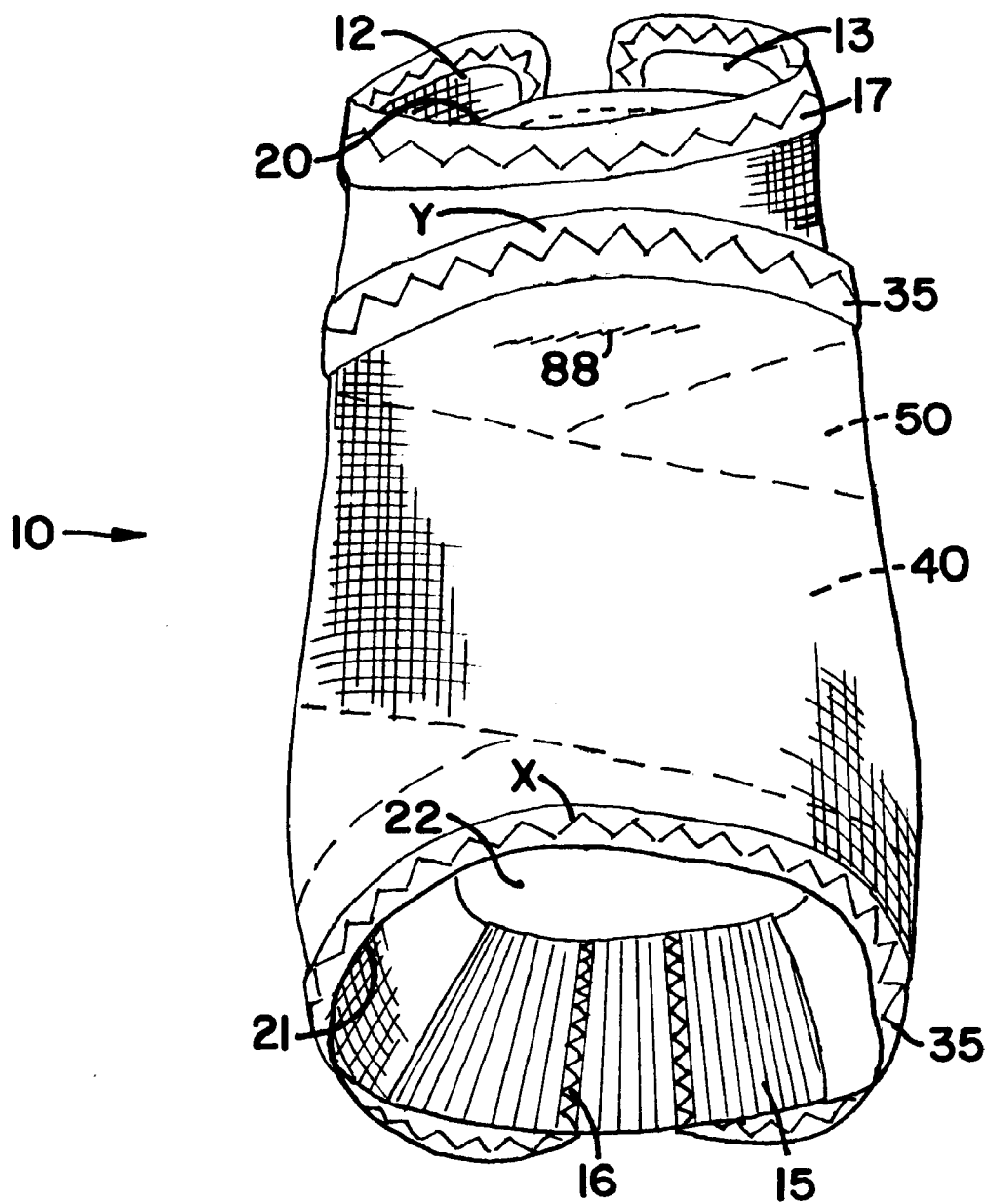
FIG. 3 is a perspective view, shown generally from below, of the ankle support brace of FIG. 1.

While in the first preferred embodiment the outer member 30 is the attachment that pre-configures the straps 40 and 50 into a figure eight configuration, it is envisioned that other optional designs would also work to pre-configured the straps 40 and 50. For instance, the first portion 11 alone shown in FIG. 1 does in fact preconfigure the straps in the figure eight position. The first end of the straps 40a and 50a are secured to the right or left side respectively by the stitching proximate the tongue 14. Then, the slots 41 and 51 provide another position of confinement to preconfigure the straps 40 and 50. Also, the strap 44 for the first strap 40 and another similar strap (not shown) for the second strap 50 confines the second end 40b and 50b in the pre-configured configuration of a figure eight. By securing the end of the straps 40a and 50a to the brace and then having an additional guide (slots 41 and 51) midway through each of the straps 40 and 50 and another attachment (strap 44) proximate the second ends 40b and 50b of the straps 40 and 50, the straps 40 and 50 stay in their pre-configured figure eight position. Further, the straps 40 and 50 are held in their pre-configured configuration at the bottom of the ankle support 10 by being secured between the bindings 35 between the first portion 11 and the outer member 30. The bindings 35 at positions X and Y, as shown in FIG. 3, are stitched to the first portion 11 thereby capturing the straps 40 and 50. The binding 35 is secured around the outer member 30 and for a distance of approximately two inches, at position X and Y, is stitched to the first portion 11. Additional stitching 88 may be used to secure the outer member 30 to the first portion 11, thereby further confining the straps 40 and 50.

While the ankle support 10 is shown as being closed by means of laces 36, it is envisioned that lace eyelets, hook/loop closures or other suitable closures may also be utilized. The straps 40 and 50 may be of a thin strong relatively non-stretchable material such as a 430 denier nylon or webbing, but could also be a material that has stretch if desired. The second ends 40b and 50b are preferably secured above the malleoli on both sides. The first ends 40a and 50a are preferably sewn or permanently attached. however, they may be releasably connected by use of Velcro® or other suitable means. the straps 40 and 50 are typically tightened to the desired tightness before the laces 36 are tightened. Also, a more standard tongue, attached only at its base, may be used as in other existing ankle braces.

By having the straps 40 and 50 in their pre-configured figure eight position, the user is able to concentrate on only securing the straps 40 and 50 to the desired tightness. The design of the straps 40 and 50, such that the second ends 40b and 50b are pulled upward, provides for an efficient and effective method of securing the straps 40 and 50 at the desired tension via the hook and loop materials 42 and 43.

Figure 5:
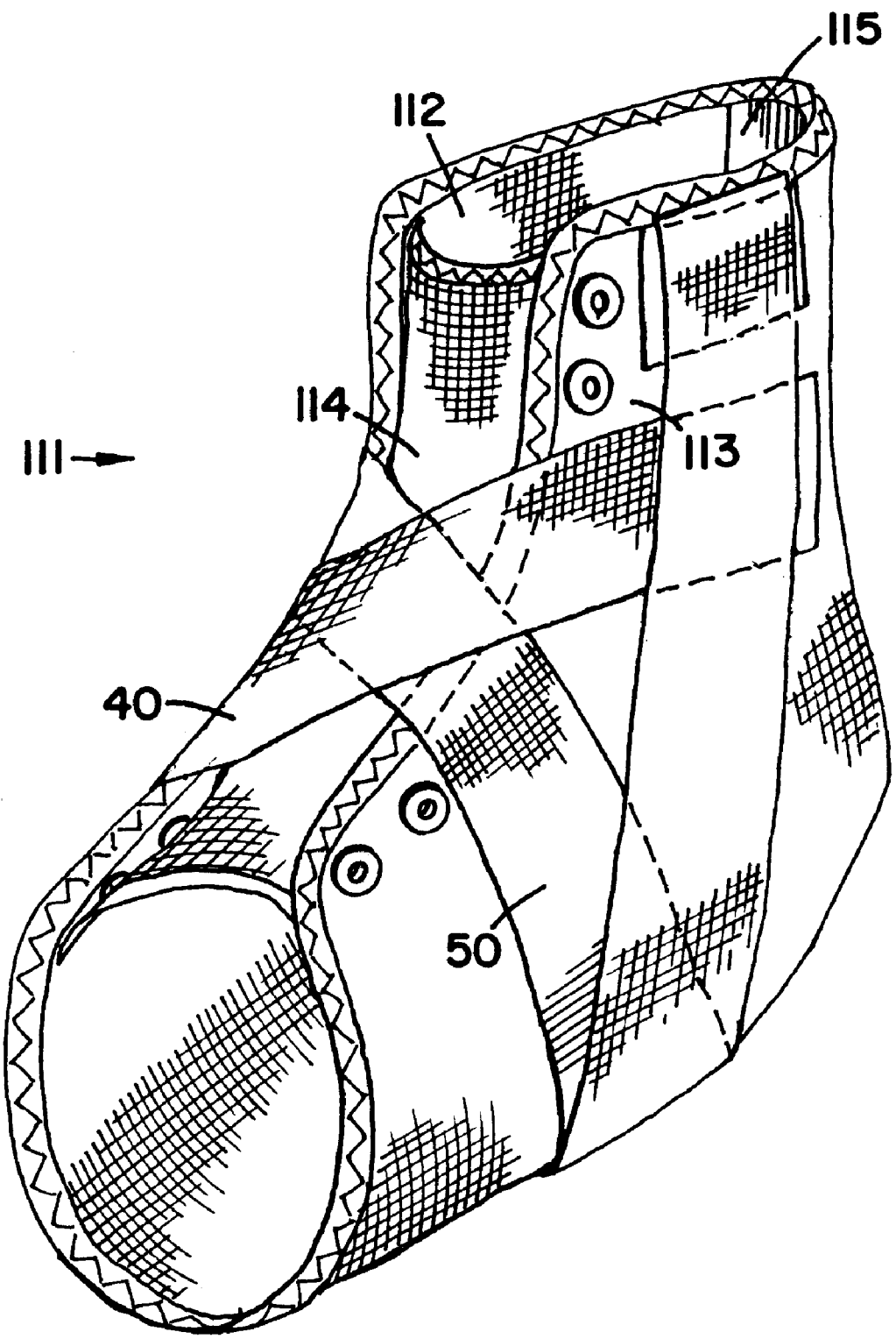
FIG. 5 is a perspective view, shown generally from the left side, of a second embodiment ankle support brace incorporating the present invention.

In a second preferred embodiment, shown in FIG. 5, the first portion 111, preferably formed from a one-piece material, includes a right side 112 and a left side 113. The right side 112 and the left side 113 are operatively connected in the front by a stretchable mesh tongue 114 and are operatively connected in the back by an elastic member 115, in a similar manner to the first preferred embodiment discussed above. This embodiment, however, does not include slots and plastic c loop guides through which the straps 40 and 50 are placed to keep them in the correct configuration. Rather, the straps 40 and 50 are placed over the mesh tongue 114 and the laces (not shown) and are kept in place by the outer member. The outer member (not shown) is the same as outer member 30 and is sewn or attached by means known in the art around the bottom and side edges to the boot-like member forming a sleeve-like guide to align and keep the straps 40 and 50 in proper configuration. The top edge and the edge proximate the eyelets of the outer member are not sewn. The sleeve-like guide formed between the boot-like member and the outer member allows the straps 40 and 50 to be pulled for adjustment purposes because the straps 40 and 50 are only secured to the boot-like member at the ends of the straps 40 and 50. In summary, the second embodiment is the same as the first embodiment with the deletion of the slots and the plastic loop guides and the position of the straps 40 and 50 over the openings 18.

Figure 7:
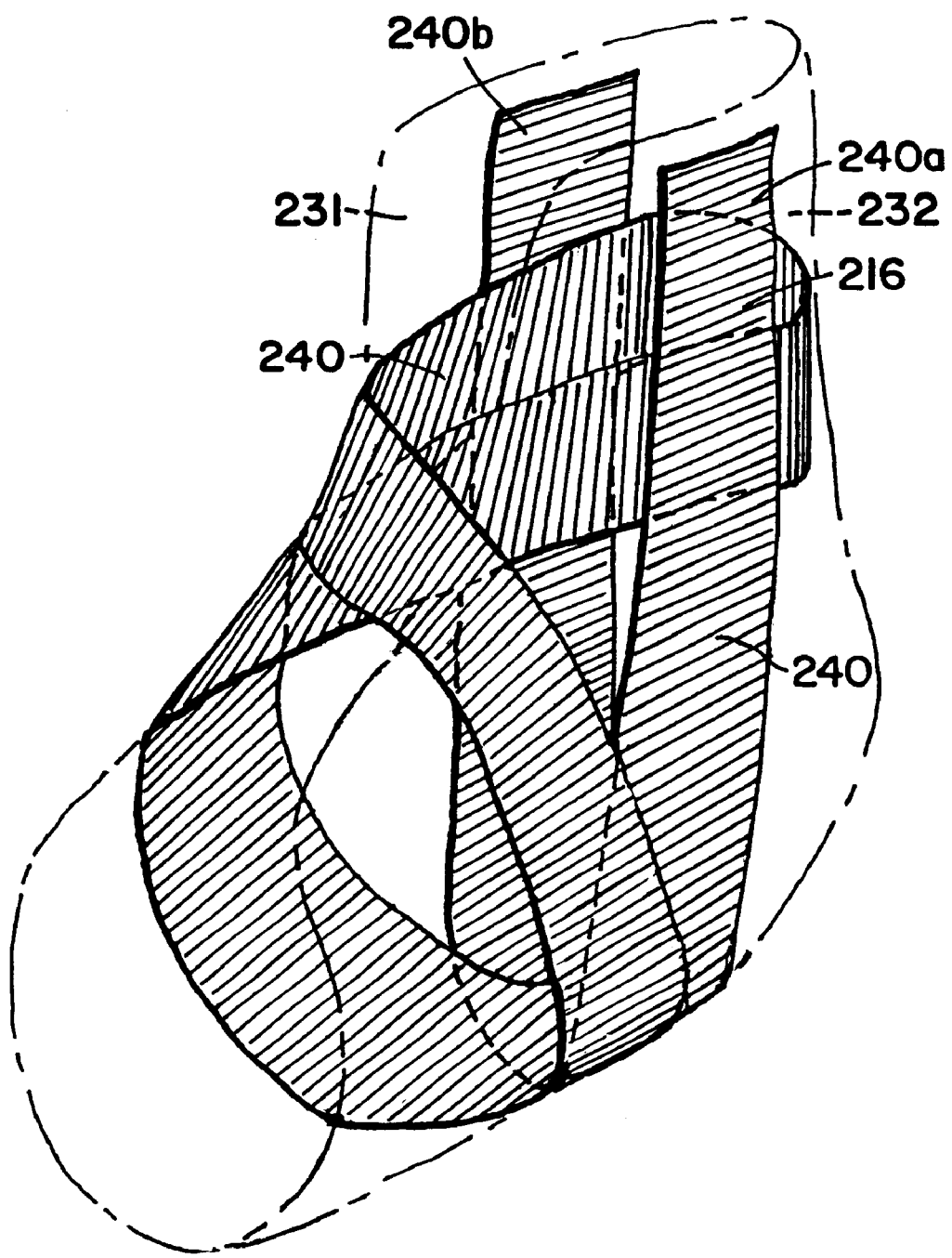
FIG. 7 is a perspective view, shown generally from the left side, of another embodiment of a strap for use with an ankle brace incorporating the present invention.

A third preferred embodiment ankle support brace utilizes a single, continuous strap member 240 to form a pre-configured figure eight member rather than utilizing two separate strap members. The strap member 240 is shown in FIG. 7. The strap member 240 includes a first end 240a and a second end 240b. First, the first end 240a is releasably secured to the top of the left side 232 of the boot-like member by suitable means known in the art. Then, the strap member 240 continues down the left side 232 and is positioned underneath the foot, over the top of the foot from the right side 231 toward the left side 232, and back behind the ankle from the left side 232. Stitching 216 may be used to secure the strap member 240 to the back of the boot-like member of the ankle support brace. The strap member 240 then continues over the top of the foot from the right side 231 thereby forming an "X" on the top of the foot. The strap member 240 is positioned underneath the foot from the left side 232 and then continues up the right side 231 of the boot-like member where the second end is releasably secured to the top of the right side 231 of the boot-like member by suitable means known in the art. Therefore, the arrangement of strap member 240 is in the same general figure eight configuration as the straps shown in the first and second embodiments but the strap is continuous by wrapping around the ankle rather than having two additional ends secured to the sides of the boot-like member. It is understood that either the single, continuous strap member 240 or the two strap members may be used to form the pre-configured figure eight member in the embodiments discussed above.

Although the preferred embodiments are shown and described independently, it is recognized that the various features may be interchanged to create additional embodiments. For example, the single, continuous strap 240 shown and described in the third embodiment may be used in the first and second embodiments rather than using the two straps 140 and 150 as shown and described. Other features may be interchanged among the embodiments according to the principles of the present invention.

The above specification, examples and data provide a complete description of the manufacture and use of the composition of the invention. Since many embodiments of the invention can be made without departing from the spirit and scope of the invention, the invention resides in the claims hereinafter appended.

We claim:

1. An ankle support for use in supporting an ankle bone and an ankle joint, comprising:
   a) a boot-like member having a sleeve portion for receiving a foot and an ankle, the boot-like member securable about the foot and the ankle, the boot-like member having a first side, a second side, a top, and a back portion;
   b) a pre-configured figure eight member having a first portion having a first end and a second portion having a second end, the first end being releasably secured to the first side of the boot-like member and the first portion adapted and configured to be positioned under the foot and extending over the top of the boot-like member and proximate the back portion, the second end of the preconfigured figure eight member being releasably secured to the second side of the boot-like member and the second portion adapted and configured to be positioned under the foot and extending over the top of the boot-like member and proximate the back portion; and
   c) an attachment operatively connected to the boot-like member, the attachment member positioned to keep the pre-configured figure eight member positioned proximate the boot-like member, the attachment positioned between and intermediate the first end and the second end, wherein the attachment maintains the preconfigured figure eight member in position prior to being secured around the ankle bone and joint, the preconfigured figure eight member remains in a preconfigured figure eight configuration during application of the ankle support.

2. The support of claim 1, further comprising a plurality of eyelets formed in the boot-like member proximate the first and second sides and laces operatively connected to the eyelets to secure the boot-like member to the foot.

3. The support of claim 1, further comprising slots formed in the boot-like member and the strap extending through the slots, and guides, each having a slot, positioned over the slots of the boot-like member through which the pre-configured figure eight member also extends.

4. The support of claim 1, wherein the first portion is secured proximate the back portion of the boot-like member and the second portion is secured proximate the back portion of the boot-like member.

5. The support of claim 1, wherein the pre-configured figure eight member is formed by a single strap member having first and second ends.

6. The support of claim 5, further comprising a first tab and a second tab operatively connected to the ends of the strap member, wherein the tabs may be pulled upward to provide tension to the strap member before the strap member is secured to the boot-like member.

7. The support of claim 1, wherein the pre-configured figure eight member is formed by a first strap member and a second strap member, the first strap member having a first end and a second end, the first end of the first strap member secured to the first side of the boot-like member and positioned over the top of the boot-like member and under the foot and extending back up the first side of the boot-like member where the second end of the first strap is releasably secured thereto, the second strap member having a first end and a second end, the first end of the second strap member secured to the second side of the boot-like member and positioned over the top of the boot-like member and being adapted and configured to be positioned under the foot and extending back up the second side of the boot-like member where the second end of the second strap is releasably secured thereto.

8. The support of claim 7, further comprising a first tab and a second tab operatively connected to the first and second strap members' second ends respectively, wherein the tabs may be pulled upward to provide tension to the strap members before the strap members are secured to the boot-like member.

9. The support of claim 7, wherein the first ends of the first and second straps are permanently secured to the boot-like member.

10. The support of claim 7, wherein either of the second ends of the first and second straps may be secured to the boot-like member to protect for inversion or eversion.

11. An ankle support for use in supporting an ankle bone and an ankle joint, comprising:
    a) a boot-like member having a sleeve portion for receiving a foot and an ankle, the boot-like member securable about the foot and the ankle, the boot-like member having a first side, a second side, a top, and a back portion;
    b) a pre-configured figure eight member having a first end and a second end;
    c) the first end releasably secured to the first side of the boot-like member and the pre-configured figure eight member adapted and configured to be extending under the foot and over the top of the boot-like member where it wraps around the ankle proximate the back portion and continues over the top of the boot-like member and adapted and configured to be positioned under the foot and then along the second side where the second end is releasably secured thereto; and
    d) an outer member secured to the boot-like member, the outer member forming a cover to hold the pre-configured figure eight member in place and prevent misalignment of the figure eight member prior to being secured around the ankle bone and joint, the preconfigured figure eight member remains in a preconfigured figure eight configuration during application of the ankle support.

12. The ankle support of claim 11, further comprising a plurality of eyelets formed in the boot proximate the first and second sides and laces operatively connected to the eyelets to secure the boot-like member to the foot.

13. The ankle support of claim 11, further comprising slots formed in the boot-like member and the pre-configured figure eight member extending through the slots, and guides, each having a slot, positioned over the slots of the boot-like member.

14. The ankle support of claim 11, wherein the pre-configured figure eight member is formed by a single strap member having first and second ends.

15. The ankle support of claim 14, further comprising a first tab and a second tab operatively connected to the ends of the strap member, wherein the tabs may be pulled upward to provide tension to the strap member before the strap member is secured to the boot-like member.

* * * * *